United States Patent
Carl et al.

(10) Patent No.: US 9,451,997 B2
(45) Date of Patent: Sep. 27, 2016

(54) FACET DEVICE AND METHOD

(71) Applicants: K2M, Inc., Leesburg, VA (US); Albany Medical College, Albany, NY (US)

(72) Inventors: Allen L. Carl, Slingerlands, NY (US); Dan Sachs, Minneapolis, MN (US); Meir Rosenberg, Newton, MA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 14/662,005

(22) Filed: Mar. 18, 2015

(65) Prior Publication Data

US 2015/0190181 A1    Jul. 9, 2015

Related U.S. Application Data

(60) Division of application No. 13/346,435, filed on Jan. 9, 2012, now Pat. No. 9,011,491, which is a continuation of application No. 12/169,370, filed on Jul. 8, 2008, now Pat. No. 8,114,158, which is a continuation-in-part of application No. 11/197,566, filed on Aug. 3, 2005, now abandoned.

(60) Provisional application No. 60/598,882, filed on Aug. 3, 2004.

(51) Int. Cl.
*A61B 17/70* (2006.01)
*A61F 2/44* (2006.01)
(Continued)

(52) U.S. Cl.
CPC ....... *A61B 17/7064* (2013.01); *A61B 17/7065* (2013.01); *A61F 2/4405* (2013.01); *A61B 17/562* (2013.01); *A61B 2017/561* (2013.01); *A61B 2017/564* (2013.01); *A61B 2562/02* (2013.01); *A61F 2/442* (2013.01); *A61F 2002/3055* (2013.01); *A61F 2002/30079* (2013.01); *A61F 2002/30242* (2013.01); *A61F 2002/30411* (2013.01); *A61F 2002/30507* (2013.01); *A61F 2002/30563* (2013.01); *A61F 2002/30566* (2013.01); *A61F 2002/30579* (2013.01); *A61F 2002/30583* (2013.01);
(Continued)

(58) Field of Classification Search
CPC ........ A61F 2/44; A61F 2/4405; A61F 2/441; A61F 2/442; A61F 2002/30682; A61F 2002/30917; A61F 2002/4666; A61F 2210/0057; A61F 2210/0066; A61B 17/7062; A61B 17/7044

See application file for complete search history.

(56) References Cited

U.S. PATENT DOCUMENTS

| | | |
|---|---|---|
| 2,774,350 A | 9/1952 | Cleveland |
| 3,242,922 A | 3/1966 | Thomas |

(Continued)

FOREIGN PATENT DOCUMENTS

| | | |
|---|---|---|
| DE | 2644735 A1 | 4/1977 |
| DE | 2845647 A1 | 5/1980 |

(Continued)

OTHER PUBLICATIONS

English translation of DE10135771A1.*

(Continued)

*Primary Examiner* — Lynnsy Summitt
(74) *Attorney, Agent, or Firm* — Carter, Deluca, Farrell & Schmidt, LLP

(57) ABSTRACT

A spine implant includes an insert positioned between facets of a zygapophyseal joint. In various embodiments, the insert is configured to exert a distraction force on one or more facets of the zygapophyseal joint. The insert may comprise one or more members having one or more opposing facet interfacing portions. A securing member is configured to interface with the insert to secure the facets.

15 Claims, 6 Drawing Sheets

(51) Int. Cl.
*A61B 17/56* (2006.01)
*A61F 2/30* (2006.01)

(52) U.S. Cl.
CPC ........... *A61F 2002/30601* (2013.01); *A61F 2002/30663* (2013.01); *A61F 2002/30677* (2013.01); *A61F 2002/30874* (2013.01); *A61F 2002/30932* (2013.01); *A61F 2210/009* (2013.01); *A61F 2210/0085* (2013.01); *A61F 2220/0025* (2013.01); *A61F 2230/0071* (2013.01); *A61F 2310/00011* (2013.01); *A61F 2310/00179* (2013.01)

(56) References Cited

U.S. PATENT DOCUMENTS

| | | |
|---|---|---|
| 3,352,226 A | 11/1967 | Nelsen |
| 3,648,691 A | 3/1972 | Lumb et al. |
| 3,693,616 A | 9/1972 | Roaf et al. |
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,125,408 A * | 6/1992 | Basser .................... A61B 5/03 600/410 |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,456,724 A * | 10/1995 | Yen .................... A61B 5/224 600/594 |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,720,746 A | 2/1998 | Soubeiran |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |

(56) References Cited

U.S. PATENT DOCUMENTS

| | | | |
|---|---|---|---|
| 5,902,305 | A | 5/1999 | Beger et al. |
| 5,910,142 | A | 6/1999 | Tatar |
| 5,928,232 | A | 7/1999 | Howland et al. |
| 5,938,663 | A | 8/1999 | Petreto |
| 5,947,967 | A | 9/1999 | Barker |
| 5,964,769 | A | 10/1999 | Wagner et al. |
| 5,976,135 | A | 11/1999 | Sherman et al. |
| 5,980,521 | A | 11/1999 | Montague et al. |
| 5,984,924 | A | 11/1999 | Asher et al. |
| 5,989,256 | A | 11/1999 | Kuslich et al. |
| 6,015,409 | A | 1/2000 | Jackson |
| 6,033,412 | A | 3/2000 | Losken et al. |
| 6,039,738 | A | 3/2000 | Sanders et al. |
| 6,053,921 | A | 4/2000 | Wagner et al. |
| 6,066,140 | A | 5/2000 | Gertzbein et al. |
| 6,077,268 | A | 6/2000 | Farris et al. |
| 6,080,156 | A | 6/2000 | Asher et al. |
| 6,083,224 | A | 7/2000 | Gertzbein et al. |
| 6,086,590 | A | 7/2000 | Margulies et al. |
| 6,101,678 | A | 8/2000 | Malloy et al. |
| 6,110,173 | A | 8/2000 | Thomas, Jr. |
| 6,123,706 | A | 9/2000 | Lange |
| 6,132,431 | A | 10/2000 | Nilsson et al. |
| 6,132,464 | A | 10/2000 | Martin |
| 6,136,000 | A | 10/2000 | Louis et al. |
| 6,176,861 | B1 | 1/2001 | Bernstein et al. |
| 6,231,575 | B1 | 5/2001 | Krag |
| 6,248,106 | B1 | 6/2001 | Ferree |
| 6,251,111 | B1 | 6/2001 | Barker et al. |
| 6,254,603 | B1 | 7/2001 | Gertzbein et al. |
| 6,261,288 | B1 | 7/2001 | Jackson |
| 6,273,914 | B1 | 8/2001 | Papas |
| 6,277,120 | B1 | 8/2001 | Lawson |
| 6,283,967 | B1 | 9/2001 | Troxell et al. |
| 6,293,949 | B1 | 9/2001 | Justis et al. |
| 6,296,643 | B1 | 10/2001 | Hopf et al. |
| 6,299,613 | B1 | 10/2001 | Ogilvie et al. |
| 6,325,805 | B1 | 12/2001 | Ogilvie et al. |
| 6,328,739 | B1 | 12/2001 | Liu et al. |
| 6,358,254 | B1 | 3/2002 | Anderson |
| 6,364,883 | B1 | 4/2002 | Santilli |
| 6,364,885 | B1 | 4/2002 | Kilpela et al. |
| 6,379,357 | B1 | 4/2002 | Bernstein et al. |
| 6,391,030 | B1 | 5/2002 | Wagner et al. |
| 6,402,749 | B1 | 6/2002 | Ashman |
| 6,402,752 | B2 | 6/2002 | Schaffler-Wachter et al. |
| 6,419,703 | B1 | 7/2002 | Fallin et al. |
| 6,423,065 | B2 | 7/2002 | Ferree |
| 6,425,920 | B1* | 7/2002 | Hamada ............. A61B 17/1604 623/17.16 |
| 6,447,448 | B1* | 9/2002 | Ishikawa .............. A61B 5/0031 128/899 |
| 6,451,019 | B1 | 9/2002 | Zucherman et al. |
| 6,458,131 | B1 | 10/2002 | Ray |
| 6,471,704 | B2 | 10/2002 | Gertzbein et al. |
| 6,478,822 | B1* | 11/2002 | Leroux .................. A61F 2/442 623/17.14 |
| 6,482,234 | B1* | 11/2002 | Weber ..................... A61F 2/441 623/17.12 |
| 6,488,683 | B2 | 12/2002 | Lieberman |
| 6,514,255 | B1 | 2/2003 | Ferree |
| 6,520,962 | B1 | 2/2003 | Taylor et al. |
| 6,537,276 | B2 | 3/2003 | Metz-Stavenhagen |
| 6,547,789 | B1 | 4/2003 | Ventre et al. |
| 6,551,320 | B2 | 4/2003 | Lieberman |
| 6,554,831 | B1 | 4/2003 | Rivard et al. |
| 6,562,038 | B1 | 5/2003 | Morrison |
| 6,565,569 | B1 | 5/2003 | Assaker et al. |
| 6,565,605 | B2 | 5/2003 | Goble et al. |
| 6,569,164 | B1 | 5/2003 | Assaker et al. |
| 6,579,292 | B2 | 6/2003 | Taylor |
| 6,579,319 | B2 | 6/2003 | Goble et al. |
| 6,582,433 | B2 | 6/2003 | Yun |
| 6,585,738 | B1 | 7/2003 | Mangione et al. |
| 6,589,243 | B1 | 7/2003 | Viart et al. |
| 6,602,254 | B2 | 8/2003 | Gertzbein et al. |
| 6,602,818 | B2 | 8/2003 | Choi et al. |
| 6,610,091 | B1 | 8/2003 | Reiley |
| 6,616,669 | B2 | 9/2003 | Ogilvie et al. |
| 6,623,484 | B2 | 9/2003 | Betz et al. |
| 6,626,906 | B1 | 9/2003 | Young |
| 6,626,909 | B2 | 9/2003 | Chin |
| 6,641,585 | B2 | 11/2003 | Sato et al. |
| 6,645,207 | B2 | 11/2003 | Dixon et al. |
| 6,651,320 | B1 | 11/2003 | Yagi et al. |
| 6,656,185 | B2 | 12/2003 | Gleason et al. |
| 6,669,729 | B2 | 12/2003 | Chin |
| 6,682,532 | B2 | 1/2004 | Johnson et al. |
| 6,682,533 | B1 | 1/2004 | Dinsdale et al. |
| 6,685,705 | B1 | 2/2004 | Taylor |
| 6,689,133 | B2 | 2/2004 | Morrison et al. |
| 6,692,495 | B1* | 2/2004 | Zacouto ................. A61B 17/70 606/247 |
| 6,706,005 | B2* | 3/2004 | Roy ..................... A61B 5/4504 600/594 |
| 6,709,435 | B2 | 3/2004 | Lin |
| 6,736,817 | B2 | 5/2004 | Troxell et al. |
| 6,749,612 | B1 | 6/2004 | Conchy et al. |
| 6,755,828 | B2 | 6/2004 | Shevtsov et al. |
| 6,773,437 | B2 | 8/2004 | Ogilvie et al. |
| 6,802,844 | B2 | 10/2004 | Ferree |
| 6,811,567 | B2 | 11/2004 | Reiley |
| 6,835,207 | B2* | 12/2004 | Zacouto ................. A61B 17/68 623/17.12 |
| 6,840,127 | B2 | 1/2005 | Moran |
| 6,860,884 | B2 | 3/2005 | Shirado et al. |
| 6,887,241 | B1 | 5/2005 | McBride et al. |
| 6,902,580 | B2 | 6/2005 | Fallin et al. |
| 6,936,072 | B2* | 8/2005 | Lambrecht ........... A61B 5/1076 623/17.11 |
| 6,946,000 | B2 | 9/2005 | Senegas et al. |
| 6,966,910 | B2 | 11/2005 | Ritland |
| 6,966,930 | B2 | 11/2005 | Arnin et al. |
| 6,974,478 | B2 | 12/2005 | Reiley et al. |
| 6,986,771 | B2 | 1/2006 | Paul et al. |
| 7,008,423 | B2 | 3/2006 | Assaker et al. |
| 7,018,379 | B2 | 3/2006 | Drewry et al. |
| 7,029,475 | B2 | 4/2006 | Panjabi |
| 7,041,136 | B2 | 5/2006 | Goble et al. |
| 7,048,736 | B2 | 5/2006 | Robinson et al. |
| 7,051,451 | B2 | 5/2006 | Augostino et al. |
| 7,074,237 | B2 | 7/2006 | Goble et al. |
| 7,083,621 | B2 | 8/2006 | Shaolian et al. |
| 7,087,056 | B2 | 8/2006 | Vaughan |
| 7,090,698 | B2 | 8/2006 | Goble et al. |
| 7,104,992 | B2 | 9/2006 | Bailey |
| RE39,325 | E | 10/2006 | Bryan |
| 7,128,743 | B2 | 10/2006 | Metz-Stavenhagen |
| 7,137,986 | B2 | 11/2006 | Troxell et al. |
| 7,160,312 | B2 | 1/2007 | Saadat |
| 7,220,262 | B1 | 5/2007 | Hynes |
| 7,261,714 | B2 | 8/2007 | Richelsoph |
| 7,270,665 | B2 | 9/2007 | Morrison et al. |
| 7,290,347 | B2 | 11/2007 | Augostino et al. |
| 7,294,129 | B2 | 11/2007 | Hawkins et al. |
| 7,316,684 | B1 | 1/2008 | Baccelli et al. |
| 7,335,203 | B2 | 2/2008 | Winslow et al. |
| 7,338,490 | B2 | 3/2008 | Ogilvie et al. |
| 7,344,539 | B2 | 3/2008 | Serhan et al. |
| 7,361,196 | B2 | 4/2008 | Fallin et al. |
| 7,367,978 | B2 | 5/2008 | Drewry et al. |
| 7,406,775 | B2 | 8/2008 | Funk et al. |
| 7,445,635 | B2 | 11/2008 | Fallin et al. |
| 7,473,267 | B2 | 1/2009 | Nguyen et al. |
| 7,473,269 | B1 | 1/2009 | Hynes |
| 7,481,828 | B2 | 1/2009 | Mazda et al. |
| 7,507,242 | B2 | 3/2009 | Triplett et al. |
| 7,524,324 | B2 | 4/2009 | Winslow et al. |
| 7,531,002 | B2* | 5/2009 | Sutton .................... A61F 2/442 606/90 |
| 7,566,345 | B1 | 7/2009 | Fallin et al. |
| 7,588,578 | B2 | 9/2009 | Triplett et al. |
| 7,588,590 | B2 | 9/2009 | Chervitz et al. |
| 7,591,836 | B2 | 9/2009 | Dick et al. |

(56) References Cited

U.S. PATENT DOCUMENTS

| | | |
|---|---|---|
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,130 B2 * | 4/2010 | Bruneau .......... A61B 17/7062 606/249 |
| 7,691,145 B2 | 4/2010 | Reiley et al. |
| 7,708,762 B2 | 5/2010 | McCarthy et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,763,075 B2 * | 7/2010 | Navarro ............ A61F 2/442 623/17.11 |
| 7,771,474 B2 | 8/2010 | Cordaro |
| 7,794,476 B2 | 9/2010 | Wisnewski |
| 7,794,478 B2 | 9/2010 | Nilsson |
| 7,794,499 B2 * | 9/2010 | Navarro ............ A61F 2/442 600/300 |
| 7,799,054 B2 | 9/2010 | Kwak et al. |
| 7,819,902 B2 | 10/2010 | Abdelgany et al. |
| 7,824,444 B2 * | 11/2010 | Biscup ............ A61F 2/442 623/17.12 |
| 7,833,252 B2 | 11/2010 | Justis et al. |
| 7,837,713 B2 * | 11/2010 | Petersen ........... A61B 17/1757 606/247 |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 7,985,256 B2 * | 7/2011 | Grotz ............ A61F 2/442 623/17.11 |
| 7,993,269 B2 * | 8/2011 | Donofrio ............ A61B 5/0031 128/903 |
| 8,012,184 B2 | 9/2011 | Schlapfer et al. |
| 8,016,859 B2 * | 9/2011 | Donofrio ............ A61B 5/0031 606/246 |
| 8,016,860 B2 | 9/2011 | Carl et al. |
| 8,021,392 B2 * | 9/2011 | Petersen ............ A61F 2/4405 606/247 |
| 8,021,400 B2 | 9/2011 | Marino et al. |
| 8,029,543 B2 | 10/2011 | Young et al. |
| 8,029,546 B2 | 10/2011 | Capote et al. |
| 8,029,566 B2 * | 10/2011 | Lozier ............ A61B 17/7275 442/209 |
| 8,034,078 B2 | 10/2011 | Laskowitz et al. |
| 8,034,080 B2 * | 10/2011 | Malandain ......... A61B 17/025 606/249 |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,057,472 B2 | 11/2011 | Walker et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,083,741 B2 * | 12/2011 | Morgan .......... A61N 1/205 606/280 |
| 8,095,198 B2 * | 1/2012 | Nycz ............ A61B 5/0031 600/348 |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,128,699 B2 * | 3/2012 | Justis ............ A61F 2/4425 600/12 |
| 8,147,524 B2 | 4/2012 | Piza Vallespir |
| 8,147,549 B2 * | 4/2012 | Metcalf, Jr. .......... A61B 5/0031 623/17.11 |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,192,495 B2 * | 6/2012 | Simpson ............ A61F 2/44 623/17.15 |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,491,572 B2 * | 7/2013 | Martinson ........... A61B 5/0031 128/903 |
| 8,518,086 B2 | 8/2013 | Seme et al. |
| 8,636,802 B2 * | 1/2014 | Serhan ............ A61B 17/7062 623/17.11 |
| 8,690,888 B2 * | 4/2014 | Stein .................. A61B 17/025 606/102 |
| 8,790,278 B2 * | 7/2014 | Walter ................ A61B 5/4504 600/587 |
| 8,828,058 B2 | 9/2014 | Elsebaie et al. |
| 8,911,448 B2 * | 12/2014 | Stein ................ A61F 2/442 606/102 |
| 8,945,133 B2 * | 2/2015 | Stein ................ A61B 5/107 600/424 |
| 8,956,418 B2 * | 2/2015 | Wasielewski ............ A61B 5/03 600/309 |
| 8,961,571 B2 * | 2/2015 | Lee .................. A61B 17/1604 606/247 |
| 8,992,620 B2 * | 3/2015 | Ashley ................ A61F 2/4455 623/17.16 |
| 9,011,491 B2 | 4/2015 | Carl et al. |
| 9,095,436 B2 * | 8/2015 | Boyden ............ A61B 17/68 |
| 2001/0037111 A1 | 11/2001 | Dixon et al. |
| 2002/0032442 A1 | 3/2002 | Altarac et al. |
| 2002/0055739 A1 | 5/2002 | Lieberman |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0186576 A1 * | 9/2004 | Biscup ............ A61F 2/442 623/17.12 |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |

(56) References Cited

U.S. PATENT DOCUMENTS

| | | |
|---|---|---|
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0085075 A1* | 4/2006 | McLeer ............. A61F 2/4405 623/17.12 |
| 2006/0089646 A1* | 4/2006 | Bonutti ............. A61B 17/0218 606/279 |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0190081 A1* | 8/2006 | Kraus ............. A61B 17/7064 623/17.11 |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0247633 A1* | 11/2006 | Winslow ............. A61B 17/025 606/247 |
| 2006/0247650 A1* | 11/2006 | Yerby ............. A61B 17/025 606/90 |
| 2006/0247773 A1* | 11/2006 | Stamp ............. A61B 5/076 623/17.11 |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0276790 A1* | 12/2006 | Dawson ............. A61F 2/4405 606/86 A |
| 2006/0293663 A1 | 12/2006 | Walkenhorst et al. |
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161993 A1 | 7/2007 | Lowery et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0179493 A1* | 8/2007 | Kim ............. A61B 17/7062 606/33 |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0065069 A1 | 3/2008 | Betz et al. |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0177392 A1* | 7/2008 | Williams ............. A61F 2/441 623/17.16 |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |

(56) References Cited

U.S. PATENT DOCUMENTS

| | | |
|---|---|---|
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0132050 A1* | 5/2009 | Holm .................. A61F 2/30942 623/17.16 |
| 2009/0194206 A1 | 8/2009 | Jeon et al. |
| 2009/0204156 A1 | 8/2009 | McClintock et al. |
| 2009/0216331 A1* | 8/2009 | Grotz .................. A61F 2/442 623/17.16 |
| 2009/0234456 A1* | 9/2009 | Nycz .................. A61F 2/442 623/17.16 |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0100185 A1* | 4/2010 | Trieu .................. A61F 2/4425 623/17.16 |
| 2010/0106192 A1 | 4/2010 | Barry |
| 2010/0137913 A1 | 6/2010 | Khatchadourian et al. |
| 2010/0168864 A1* | 7/2010 | White .............. A61B 17/06114 623/18.11 |
| 2010/0191100 A1* | 7/2010 | Anderson .............. A61B 5/055 600/424 |
| 2010/0204802 A1* | 8/2010 | Wilson .................. A61B 5/0031 623/23.6 |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2012/0221057 A1 | 8/2012 | Zhang et al. |
| 2013/0079793 A1* | 3/2013 | Stein .................. A61F 2/4657 606/102 |
| 2013/0103156 A1* | 4/2013 | Packer .................. A61F 2/442 623/17.16 |
| 2013/0123851 A1 | 5/2013 | Seme et al. |
| 2013/0123853 A1 | 5/2013 | Seme et al. |
| 2013/0150970 A1* | 6/2013 | Thaiyananthan ....... A61F 2/442 623/17.16 |
| 2013/0184757 A1 | 7/2013 | Seme et al. |
| 2013/0204157 A1* | 8/2013 | Clark .................. A61B 5/4576 600/547 |
| 2013/0211455 A1 | 8/2013 | Seme |
| 2013/0231703 A1 | 9/2013 | Seme et al. |
| 2015/0257799 A1* | 9/2015 | Janna .................. A61F 5/05 606/328 |
| 2015/0282797 A1* | 10/2015 | O'Neil .................. A61B 17/025 606/279 |
| 2015/0297362 A1* | 10/2015 | Singh .................. A61F 2/4657 623/22.15 |

FOREIGN PATENT DOCUMENTS

| | | | |
|---|---|---|---|
| DE | 10135771 | * 2/2003 | ......... A61B 17/7064 |
| EP | 0260044 A1 | 3/1988 | |
| EP | 0322334 A1 | 6/1989 | |
| EP | 0418387 A1 | 3/1991 | |
| EP | 1281361 A1 | 2/2003 | |
| FR | 2697744 A1 | 5/1994 | |
| FR | 2736535 A1 | 1/1997 | |
| FR | 2781359 A1 | 1/2000 | |
| FR | 2801492 A1 | 6/2001 | |
| FR | 2872021 A1 | 12/2005 | |
| FR | 2900563 A1 | 11/2007 | |
| GB | 780652 A | 8/1957 | |
| SU | 888968 A1 | 12/1981 | |
| WO | 9213496 A1 | 8/1992 | |
| WO | 2004017705 A2 | 3/2004 | |
| WO | 2006010844 A1 | 2/2006 | |
| WO | 2006017641 A2 | 2/2006 | |
| WO | 2006136937 A2 | 12/2006 | |
| WO | 2007051924 A1 | 5/2007 | |
| WO | 2008086467 A2 | 7/2008 | |
| WO | 2008154313 A1 | 12/2008 | |
| WO | 2010053662 A1 | 5/2010 | |
| WO | 2010056650 A1 | 5/2010 | |
| WO | 2010111500 A2 | 9/2010 | |

OTHER PUBLICATIONS

Berry, James L. et al., A Morphometric Study of Human Lumbar and Selected Thoracic Vertebrae, 12 Spine 362 (1987).

Fujita, Masaru et al., A Biomechanical Analysis of Sublaminar and Subtransverse Process Fixation Using Metal Wires and Polyethylene Cables, 31 Spine 2202 (2006).

Girardi, Federico R et al., Safety of Sublaminar Wires With Isola Instrumentation for the Treatment of Idiopathic Scoliosis, 25 Spine 691 (2000).

International Application No. PCT/US2008/065979, filed Jun. 5, 2008, entitled Medical Device and Method to Correct Deformity.

International Application No. PCT/US2009/063833, filed Nov. 10, 2009, entitled Growth Directed Vertebral Fixation System With Distractible Connector(s) and Apical Control.

International Application No. PCT/US2010/028684, filed Mar. 25, 2010, entitled Semi-Constrained Anchoring System.

International Search Report and Written Opinion issued in PCT/US2005/027692, mailed May 19, 2008, 4 pages.

International Search Report and Written Opinion issued in PCT/US2008/065979, mailed Oct. 2, 2008, 7 pages.

International Search Report and Written Opinion issued in PCT/US2009/063833, mailed Mar. 15, 2010, 14 pages.

International Search Report and Written Opinion issued in PCT/US2010/028684, mailed Sep. 28, 2010, 19 pages.

International Search Report and Written Opinion issued in PCT/US2010/036375, mailed Sep. 10, 2010, 16 pages.

International Search Report and Written Opinion issued in PCT/US2010/047117, mailed Dec. 2, 2010.

(56) References Cited

OTHER PUBLICATIONS

International Search Report and Written Opinion issued in PCT/US2011/049693, mailed Nov. 15, 2011, 16 pages.
Invitation to Pay Additional Fees and Partial Search Report issued in PCT/US2010/028684, mailed Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and in Vitro Determination of the Axial Rotational Axis of the Human Thoracic Spine, 31 Spine E984 (2006).
Rajasekaran, S. et al., Eighteen-Level Analysis of Vertebral Rotation Following Harrington-Luque Instrumentation in Idiopathic Scoliosis, 76 J Bone Joint Surg Am. 104 (1994).
U.S. Appl. No. 12/411,558, filed Mar. 26, 2009, entitled Alignment System With Longitudinal Support Features.
U.S. Appl. No. 12/411,562, filed Mar. 26, 2009, entitled Semi-Constrained Anchoring System.
U.S. Appl. No. 12/485,796, filed Jun. 16, 2009 entitled Deformity Alignment System With Reactive Force Balancing.
U.S. Appl. No. 12/560,199, filed Sep. 15, 2009, entitled Growth Modulation System.
Wenger, Dennis R. et al., Biomechanics of Scoliosis Correction by Segmental Spinal Instrumentation, 7 Spine 260 (1982).
White III, Augustus A. et al., Biomechancis of the Spine 28-29, Tbl. 1-5 (2d ed. 1990).
European Search Report issued in EP Application No. 12154799, completed Mar. 2, 2012, 9 pages.
International Search Report and Written Opinion issued in PCT/US2012/065262, mailed Feb. 5, 2013, 8 pages.
International Search Report and Written Opinion issued in PCT/US2012/040493, mailed Aug. 21, 2012, 15 pages.
International Search Report and Written Opinion issued in PCT/US2013/065488, mailed Feb. 18, 2014, 10 pages.
Eglin, D. et al., "Degradable Polymeric Materials for Osteosynthesis: tutorial", European Cells and Materials, vol. 16, 2008, pp. 80-91.
Girardi, Federico P. et al., Safety of Sublaminar Wires With Isola Instrumentation for the Treatment of Idiopathic Scoliosis, 25 SPINE 691 (2000).
International Application No. PCT/US2010/28684, filed Mar. 25, 2010, entitled Semi-Constrained Anchoring System.

* cited by examiner

FACET DEVICE AND METHOD

CROSS-REFERENCE TO RELATED APPLICATIONS

The present application is a divisional of application Ser. No. 13/346,435, filed Jan. 9, 2012 and entitled "Facet Device and Method," which is a continuation of application Ser. No. 12/169,370, filed Jul. 8, 2008 and entitled "Facet Device and Method," now U.S. Pat. No. 8,114,158, which is a continuation-in-part of application Ser. No. 11/197,566, filed Aug. 3, 2005 and entitled "Facet Device and Method," now abandoned, which claims the benefit of U.S. Provisional Application No. 60/598,882, filed Aug. 3, 2004 and entitled "Spine Treatment Devices and Methods," all of which are incorporated by reference herein in their entireties for all purposes.

FIELD OF THE INVENTION

The invention relates to devices to treat the spine, in particular in association with a facet joint, including but not limited to spinal stabilization devices, spinal distraction devices, spinal prostheses, devices to treat pain associated with the spine, and other spinal treatment devices.

DESCRIPTION OF THE RELATED ART

Certain spine conditions, defects, deformities (e.g., scoliosis) as well as injuries may lead to structural instabilities, nerve or spinal cord damage, pain or other manifestations. Back pain (e.g., pain associated with the spinal column or mechanical back pain) may be caused by structural defects, by injuries or over the course of time from the aging process. For example, back pain is frequently caused by repetitive and/or high stress loads on or increased motion around certain boney or soft tissue structures. The natural course of aging leads to degeneration of the disc, loss of disc height, and instability of the spine among other structural manifestations at or around the spine. With disc degeneration, the posterior elements of the spine bear increased loads with disc height loss, and subsequently attempt to compensate with the formation of osteophytes and thickening of various stabilizing spinal ligaments. The facet joints may develop pain due to arthritic changes caused by increased loads. Furthermore, osteophytes in the neural foramina and thickening of spinal ligaments can lead to spinal stenosis, or impingement of nerve roots in the spinal canal or neural foramina. Scoliosis also creates disproportionate loading on various elements of the spine and may require correction, stabilization or fusion.

Pain caused by abnormal motion of the spine has long been treated by fixation of the motion segment. Spinal fusion is one way of stabilizing the spine to reduce pain. In general, it is believed that anterior interbody or posterior fusion prevents movement between one or more joints where pain is occurring from irritating motion. Fusion typically involves removal of the native disc, packing bone graft material into the resulting intervertebral space, and anterior stabilization, e.g., with intervertebral fusion cages or posterior stabilization, e.g., supporting the spinal column with internal fixation devices such as rods and screws. Internal fixation is typically an adjunct to attain intervertebral fusion. Many types of spine implants are available for performing spinal fixation, including the Harrington hook and rod, pedicle screws and rods, interbody fusion cages, and sublaminar wires.

Alternatives have been proposed and tested to replace the need for spinal fusion to treat patients with back pain. These implants include artificial discs and artificial nucleus technologies that preserve motion. However, these implants do not directly address the forces borne by the facet joints.

The facet joints provide a means for load transmission, support and motion of the posterior spinal column. Disc height loss from degenerative disc disease and aging leads to increased load on the facet joints, which can lead to arthritic, painful, degenerative changes.

Often over the course of degenerative disc disease there is a narrowing of the neural foramen through which the nerves exit the spine. In addition to the degeneration of discs causing the narrowing of the foramen, there is also calcification around the foramen causing further narrowing or stenosis resulting in pain to the patient. Currently, these conditions may be treated by removing some or all of the lamina (laminectomy) or posterior bone adjacent or around the stenotic neural foramen Given that the facet joint and its environs is a source of pain for some patients, some procedures have been developed or proposed to relieve pain associated with the facet joint. Partial or complete removal of the pathological facets, and replacement with a mechanical joint that preserves motion similar to a facet has been proposed. Additionally, individual degenerative facet articulations have been replaced with caps.

It would be desirable to provide improved devices and methods for relieving pain associated with the facet joints.

Spinal stenosis pain or from impingement of nerve roots in the neural foramina has been treated by laminectomy and foraminotomy, and sometimes reinforced with rod and screw fixation of the posterior spine.

More recently, as an alternative to laminectomies and related procedures, implants have been proposed that distract the spine from a posterior approach. In particular, a wedge-like implant inserted between two adjacent spinous processes has been proposed to relieve pressure on spinal nerves and nerve roots. A kyphosis is induced, which opens the space of the spinal canal and neural foramen, thereby reducing the effect of spinal stenosis. However, this type of distraction of adjacent spinous processes is suboptimal for several reasons: The resulting kyphosis is non-physiologic, leading to increased load on the anterior portion of the disc and the vertebral bodies. This can increase the risk of disc degeneration and vertebral compression fracture. The implant tends to bend the spine forward. The spinous processes may fracture due to the distraction forces of the wedge implant. Bone may collapse around the spinous process. The implant may weaken, tear, or stretch stabilizing ligaments of the spine, such as the supraspinous ligament, interspinous ligament, ligamentum flavum, posterior longitudinal ligament, or capsule of the zygapophyseal joint. The amount of distraction is not adjustable to the specific amount of stenosis, and cannot be easily readjusted months to years after the device has been implanted.

It would accordingly be desirable to provide a distraction device that reduces or avoids some or all of these issues.

Pain due to instability of the spine has also been treated with dynamic stabilization of the posterior spine, using elastic bands that connect pedicles of adjacent vertebrae.

The typical techniques for fusion, decompression, and dynamic stabilization require open surgical procedures with removal of stabilizing muscles from the spinal column, leading to pain, blood loss, and prolonged recovery periods after surgery due in part to the disruption of associated body structures or tissue during the procedures.

Accordingly, it would be desirable to provide less invasive devices and methods for treating pain or discomfort associated with the spinal column. It would also be desirable to provide such devices and methods that are less damaging to associated tissue.

Spine surgeons commonly use metallic or polymeric implants to effect or augment the biomechanics of the spine. The implants frequently are attached or anchored to bone of the spine. Sites typically considered appropriate for boney attachment have high density or surface area, such as, for example, the pedicle bone, the vertebral body or the cortical bone of the lamina. The spinous process contains thin walls of cortical bone, and thus, has been considered as not ideal for anchoring spinal implants as they may not support the implants under physiologic loads, or the intermittent high loads seen in traumatic situations. Fixation has been attempted from spinous process to spinous process with poor results.

A translaminar facet screw as used by some surgeons goes through the base of spinous process to access the cancellous bone of the lamina. A disadvantage of this device is that it is not suitable for attaching to a pedicle screw and the depth and angle during deployment can be very difficult to track or visualize, thus increasing the possibility that the screw would extend into the spinal canal. A facet screw is screwed between opposing facets of a zygapophyseal joint.

SUMMARY OF THE INVENTION

One aspect of the present invention is directed to providing a device and method for alleviating discomfort and or deformity associated with the spinal column. Another aspect of the present invention is directed to providing a minimally invasive implant and method for alleviating discomfort associated with the spinal column. Another aspect of the present invention provides an anchoring device and method that requires less surrounding tissue damage or disruption. Other aspects of the invention may supplement or bear load for degenerated or painful joints, e.g., the facet joint.

One aspect of the invention provides for repair or reconstruction of a dysfunctional facet joint. For example, by entering the capsule of the facet joint, creating a space between articulating facets by removing synovium, cartilage, and some bone from within the zygapophysial joint, and, then, inserting a motion preserving prosthesis. Motion preserving prostheses may include a smooth and/or curved surface, a sphere, an egg shaped/oval implant, or a self contained "ball and socket" joint. Magnetic plates with like poles facing each other may be attached to interfacing articulating portions of the facets. Attachment of the motion preserving prosthesis may involve extensions from the prosthesis that partially or completely penetrate each of the facets.

Another aspect of the invention provides for repairing the encapsulating ligaments with suture, adhesive, a patch, or other materials after a capsule of the zygapophysial joint has been invaded for tissue removal and insertion of a prosthesis. One aspect of the invention includes an elastic encapsulating wrap used to stabilize the facet joints.

According to an embodiment of the invention, a facet distraction implant is provided for maintaining a space that is formed between the facet articulations of adjacent vertebrae when the joints are distracted. The facets may be distracted using a known distraction method or technique and an implant may be placed between the facets. A securing device according to the invention may be positioned to anchor each of the facet articulations of a facet joint to each other in distraction to maintain the opening of the corresponding neural foramen. The prosthesis may include a distraction element that exerts a distracting force on the joint.

Various aspects of the invention are set forth in the description and/or claims herein.

DETAILED DESCRIPTION OF THE PREFERRED EMBODIMENT

FIGS. 1-5 illustrate facet repair prostheses in accordance with an embodiment of the invention. Prosthesis 410 comprises a ball bearing 411 implanted between the caudal and the cephalic facets 412, 413 of the zygapopyhseal joint. (FIG. 1) The joint is prepared by removing soft tissue between the joints and creating a concavity on adjacent facet plates for receiving the ball bearing.

Figure 1:
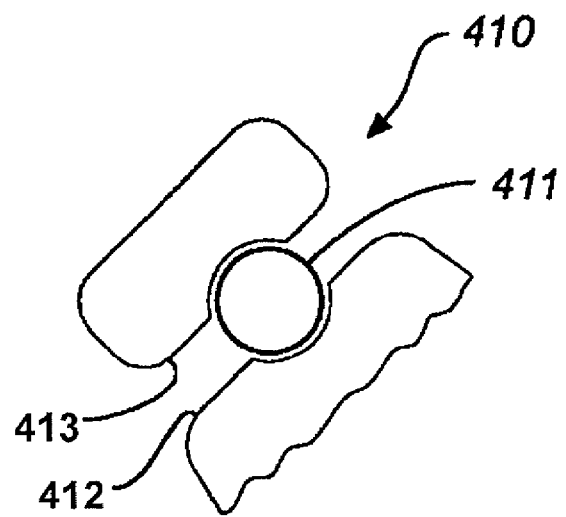
FIG. 1 is a schematic side view of a facet implant in accordance with the invention.
Figure 2:
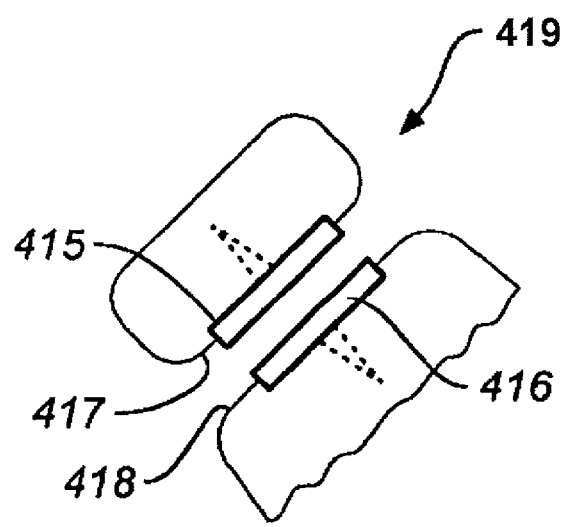
FIG. 2 is a schematic side view of a facet implant in accordance with the invention.

In FIG. 2, magnets 415, 416 including smooth interacting bearing surfaces are respectively screwed into the cephalic and caudal facets 417, 418 of the zygapopyhseal joint 419. The magnets 415, 416 are oriented so that like poles face each other (e.g. North-North or South-South) to provide a distraction force at the joint. The magnets may have a center hole through which a rod is inserted to resist the tendency of one magnet to move relative to the other. Each end of the rod may have a diameter larger than the center holes. This system may be used in other joints in the body to maintain separation between the joints.

Figure 3:
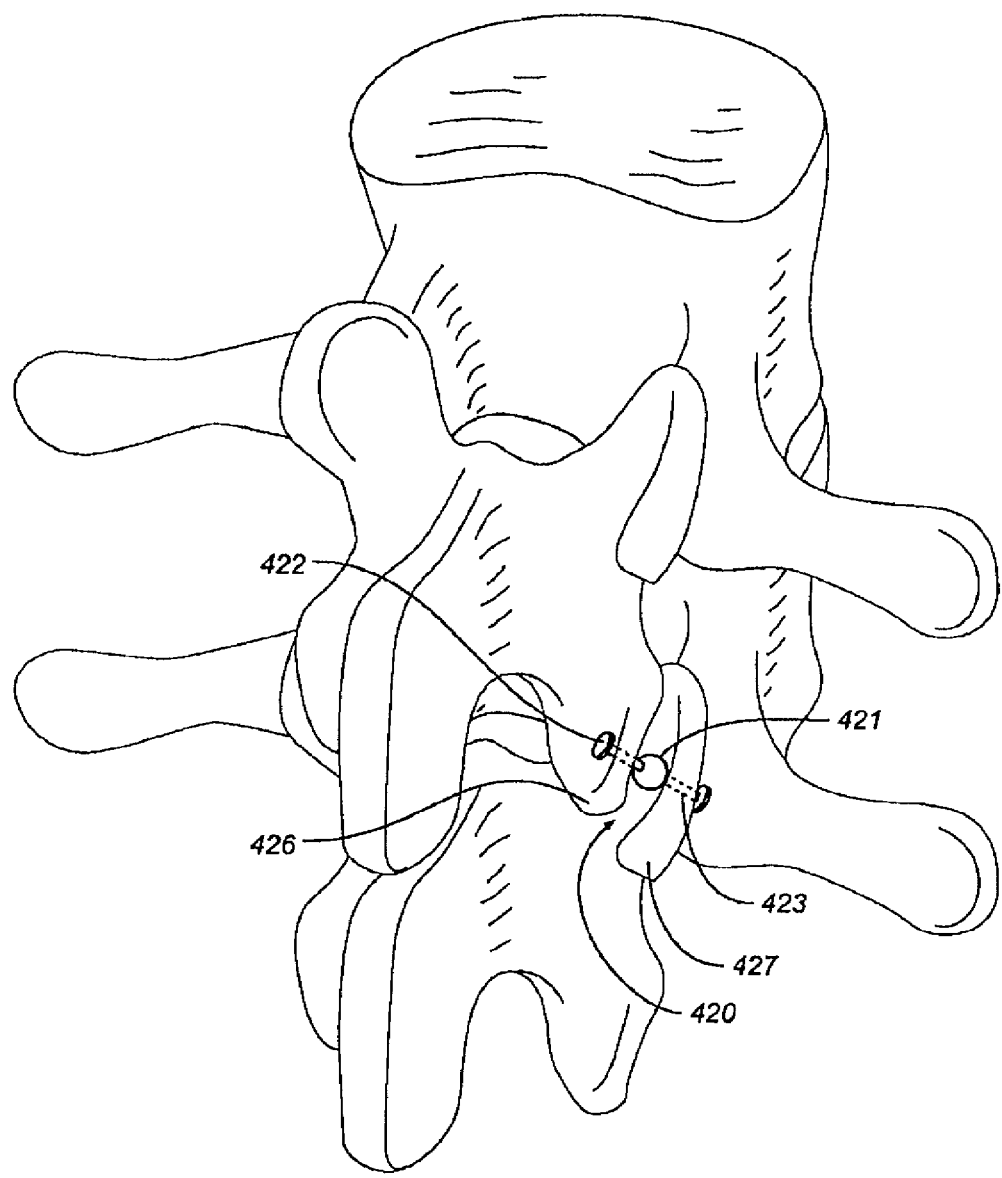
FIG. 3 is a schematic posterior lateral perspective view of a facet implant in accordance with the invention.

Referring to FIG. 3, a joint prosthesis 420 is positioned between the cephalic and caudal facets 426, 427. The prosthesis comprises a ball 421 providing a bearing surface for the motion of the facets 426, 427, and opposing posts 422, 423 screwed in or otherwise implanted in the facets 426, 427, respectively for securing the ball 421 within the joint. The ball 421 may include openings for receiving the posts, e.g., in a tapered interference type fitting, to secure the posts 422, 423 to the ball 421 and to secure the ball 421 within the joint.

This facet repair may be performed percutaneously or via minimally invasive surgical techniques, for example using percutaneously positioned distracting instruments to distract the joint, for example, an expanding balloon or forceps like distractors. Using a hollow needle percutaneously positioned into the joint, an expandable or self-expanding facet distraction implant may be placed in position through the hollow lumen of the needle into the joint. A polymer material may be injected into the joint through a percutaneously inserted needle.

Figure 4:
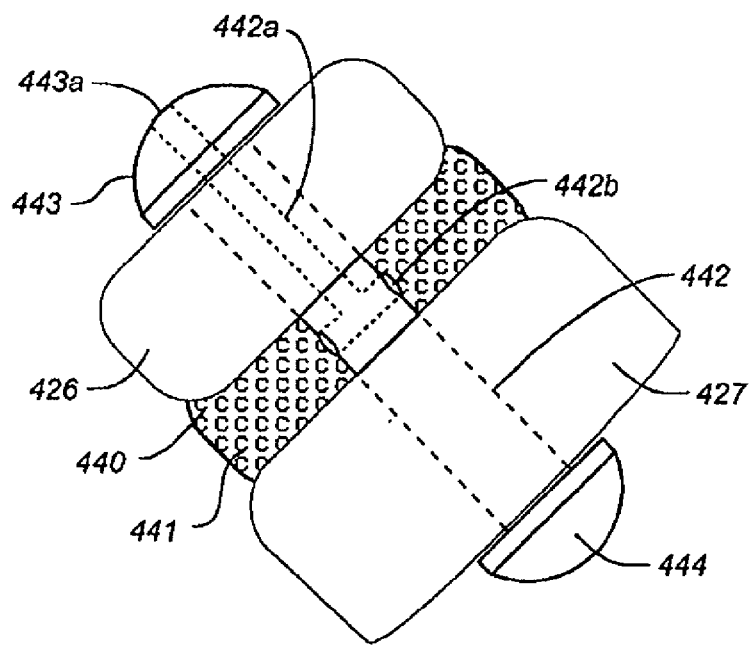
FIG. 4 is a side partial cross section of a facet implant in accordance with the invention.

FIG. 4 illustrates a material 440 such as a polymer injected between the cephalic and caudal facets 426, 427. The material 440 forms a flexible member 441 that allows some movement of the joint due to the flexible properties and/or the shape that permit articulation of the joint. A securing member 442 extends through the facets 426, 427 and the material 440 to further hold the member 441 in place in the joint capsule and/or to prevent implant extrusion. The securing member 442 includes anchors 443, 444 that anchor to the outside or within the facets 426, 427 to hold the securing member 442 in place while permitting some motion for example through spacing at or in the joint. The securing member 442 may for example, comprise a screw, or may be constructed of a flexible material such as a flexible polymer. The securing member may also comprise a band constructed of fibers strands such as Kevlar™, polypropylene or polyethylene, or constructed of a fiber reinforced polymer. The anchors 443, 444 may be of a material such as titanium, or PEAK that may be screwed or crimped on to the securing member 442. The polymer may be injected into the joint capsule into opening 443a in the anchor 443, through a lumen 442a in the securing member 442 and through holes 442b or pores in the securing member 442. This may be done when the joint is distracted or otherwise positioned as desired.

Figure 5:
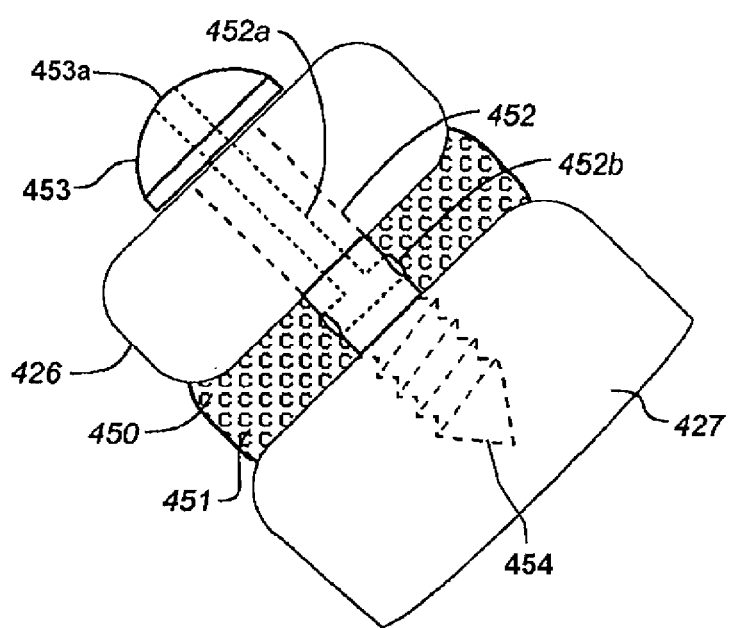
FIG. 5 is a side partial cross section of a facet implant in accordance with the invention.

FIG. 5 illustrates a material 450 such as a polymer injected between the cephalic and caudal facets 426, 427. The material 450 forms an implant 451 that allows some movement of the joint due to the flexible properties and/or a shape that permits articulation of the joint. A securing member 452 extends through the facets 426, 427 and material 450 to further hold the implant 451 in place in the joint capsule. The securing member 452 includes an anchor 453 that anchors the member to the outside or within the facet 426, (or alternatively to the outside or within the facet 427) to hold the securing member 452 in place. The securing member 452 further includes a tapered end that allows the securing member 452 to be inserted through the joint capsule and anchored into facet 427. The securing member may be a screw with a threaded tip 454 that screws into the bone. The securing member can further include a flexible portion that allows some movement of the securing member and joint. The anchor 453 may include an opening 453a into a lumen 452a in the securing member 452, for injecting a polymer into a lumen 452a in the member and then through holes 452b into the joint capsule to form the implant 451.

According to the invention, a facet joint device as described herein may be used in combination with an artificial disc or other spinal implants, e.g., to maintain the integrity of the facets. The facet joint distraction or replacement devices and procedures described herein may be used in conjunction with anteriorly placed implants, e.g., in a load sharing arrangement. The facet joint resurfacing, distraction or augmentation as well as the anterior implants may be used with a process to pedicle distraction or stabilizing device as described herein. Various spinal implants may also be used with facet resurfacing, facet distraction or augmentation procedures.

In accordance with one aspect of the invention, narrowing or stenosis of the neural foramen may be treated using a device configured to distract the facet joint. Accordingly, a distraction system is provided for distracting the facet joint.

Figure 6:
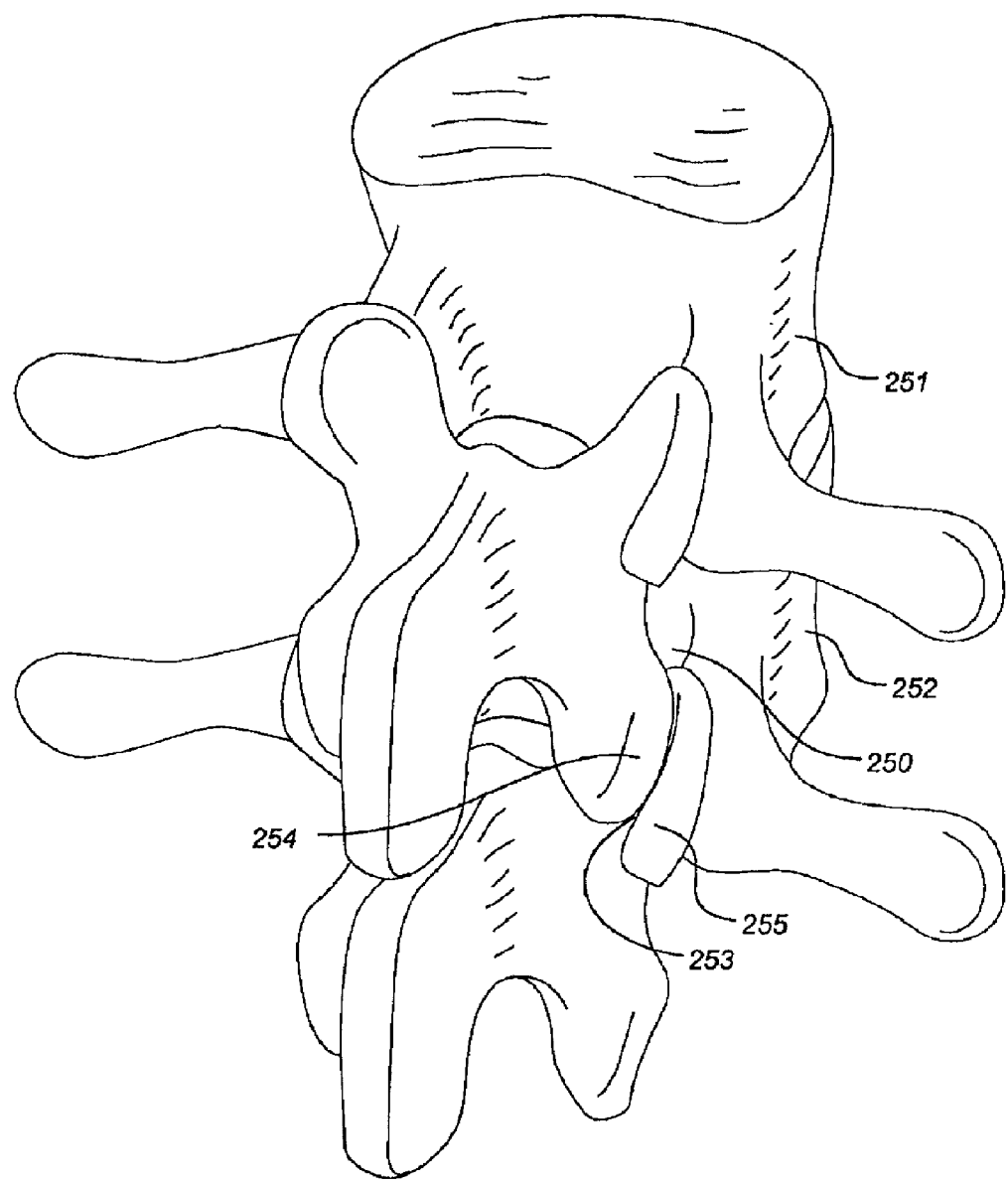
FIG. 6 is a schematic posterior lateral perspective view of a stenotic neural foramen of a posterior spine.

Referring to FIG. 6, a portion of the spine is illustrated with adjoining vertebrae prior to distraction. The neural foramen 250 between a first vertebra 251 and a second vertebra 252 is stenotic. At the zygapophyseal joint capsule 253, there is no gap between the cephalic and caudal facets 254, 255.

Figure 7:
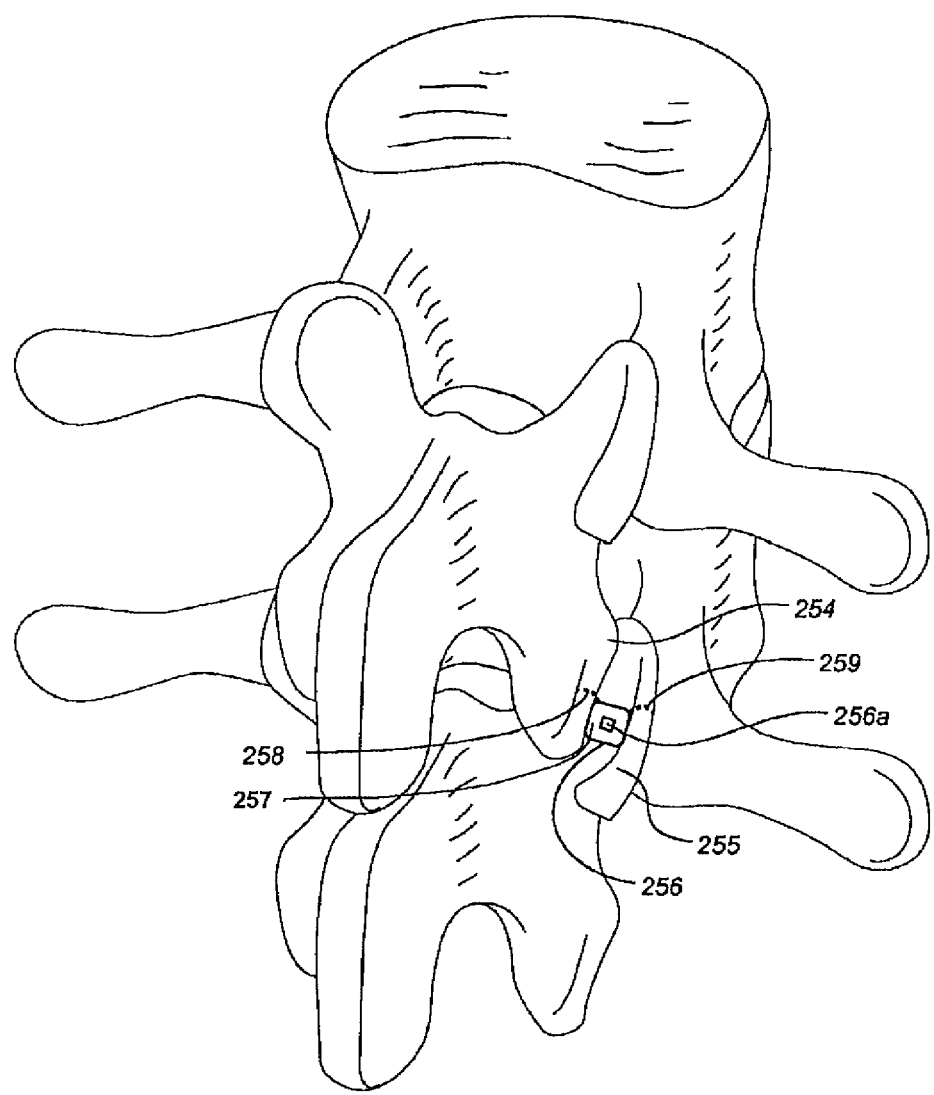
FIG. 7 is a schematic posterior lateral view of a facet implant in accordance with the invention.

Referring to FIG. 7, the portion of the spine of FIG. 6 is illustrated with a facet distracter implant 256 in place between the cephalic facet 254 and the caudal facet 255. The implant 256 comprises a distracting portion 257 and anchors 258, 259 comprising barbs or bone anchors. The distracting portion may include a distracting element as described with respect to FIGS. 8-13 herein. The anchor 258 is positioned in bone above the cephalic facet 254 while the anchor 259 is positioned in the bone below the caudal facet 255. The facet distracter implant 256 includes a sensor 256a, the type of which may be selected to sense one of a number of different parameters. Pressure sensors, strain gauges, or other sensors may be used to sense load seen by the facet joint. This information may be used to monitor the condition of the facet joint or determine if fusion may be necessary. The other facet joint implants described herein may also include similar sensors.

The procedure for implanting the device generally includes opening the zygapophyseal joint capsule with a scalpel. Then the adjacent vertebrae are distracted by one of a number of known distraction methods or by distracting the joint mechanically using devices such as a wedge or expanding rod or balloon between adjacent spinous processes, or between other parts of adjacent vertebrae. The tissue between the facets 254, 255 is then debrided and/or denervated. The implant is then inserted between the facets 254, 255 after the joint is distracted. The anchors 258, 259 engage the interfacing portions of the bone of the facets 254, 255.

Figure 8:
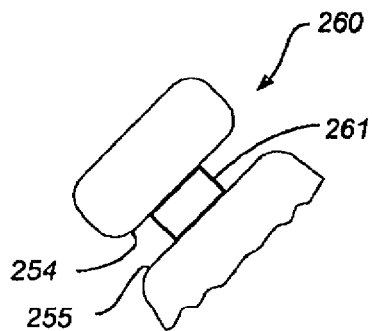
FIG. 8 is a side schematic view of a facet implant in accordance with the invention.
Figure 9:
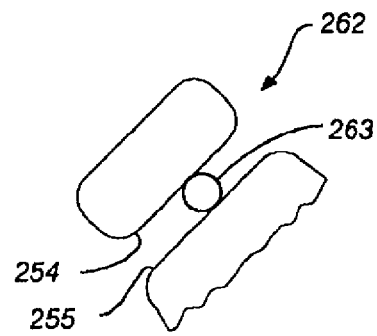
FIG. 9 is a side schematic view of a facet implant in accordance with the invention.
Figure 10:
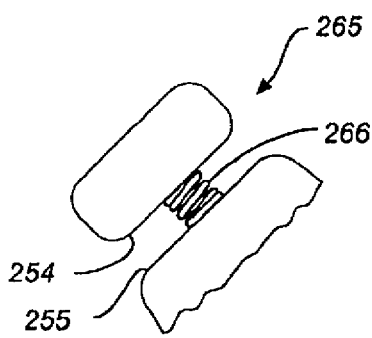
FIG. 10 is a side schematic view of a facet implant in accordance with the invention.
Figure 11:
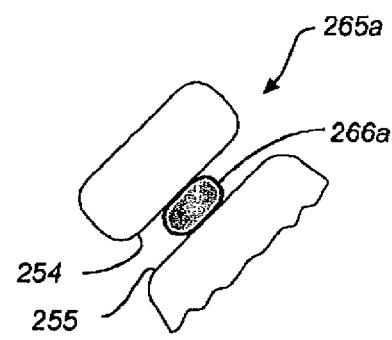
FIG. 11 is a side schematic view of a facet implant in accordance with the invention.
Figure 12:
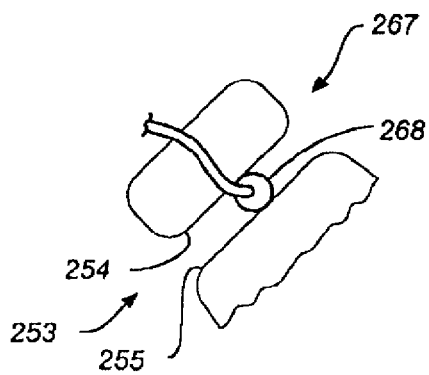
FIG. 12 is a side schematic view of a facet implant in accordance with the invention.
Figure 13:
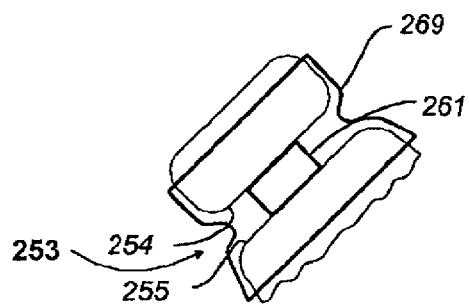
FIG. 13 is a side schematic view of a facet implant in accordance with the invention.

FIG. 8 illustrates a distracter implant 260 positioned between facets 254, 255. The distracter implant 260 comprises a block 261 wedged between the facets 254, 255. In FIG. 9 an alternative distracter 262 implant comprises a ball 263. In FIG. 10 an active distracter implant 265 comprise a coiled spring 266. In FIG. 11, the distracter implant 265a comprises an expandable polymer 266a, e.g., a hydrogel or expandable gel foam. In FIG. 12 the distracter implant 267 comprise an expandable member 268 that may be expanded to distract the joint 253 by inflating with a curable polymer, a liquid, gas or other material. The distraction may occur after implantation to adjust the level of distraction. The expandable member may also be adjusted after implanting by increasing or removing the inflation medium, e.g. using a needle or accessing the member through a one-way valve. FIG. 13 illustrates a shrink-wrap 269 placed partially around the joint 253. The shrink-wrap or other material comprises, e.g., a Dacron material that holds the block 261 or other implant in place between facets 254, 255. The material may encourage ingrowth of tissue. The material may be coated with a material that reduces tissue ingrowth to permit the joint to move or reduces adhesions to prevent pain. The material may include burrs or barbs that secure the material to the bone or it may be secured, e.g. with suture anchors. The implants may be constructed, for example, of a metal, polymer or ceramic, may be coated or imbedded with therapeutic agents (e.g. a steroid or lidocaine) or other material.

What is claimed is:

1. A facet implant comprising:
    an insert positionable between a first facet of a facet joint and a second facet of the facet joint, the insert configured to exert a distraction force on the first and second facets:
    an anchor connected to the insert and configured to secure to one of the first and second facets;
    a sensor coupled to the insert and configured to sense load on the facet joint; and
    a shrink-wrap material secured at least partially around the insert,
    wherein the shrink-wrap material includes burrs or barbs.

2. The facet implant of claim 1, wherein the anchor includes a bone anchor.

3. The facet implant of claim 1, wherein the anchor includes a barb.

4. The facet implant of claim 1, further including a second anchor connected to the insert and configured to secure to the other of the first and second facets.

5. The facet implant of claim 1, wherein the insert includes a block configured to wedge between the first and second facets.

6. The facet implant of claim 1, wherein the insert includes a ball.

7. The facet implant of claim 1, wherein the insert includes a coiled spring.

8. The facet implant of claim 1, wherein the insert includes an expandable polymer.

9. The facet implant of claim 8, wherein the expandable polymer includes a hydrogel, a gel foam, or combination thereof.

10. The facet implant of claim 1, wherein the insert is configured to inflate and distract the facet joint when the insert receives an inflation medium therein while positioned within a facet joint capsule defined between the first and second facets, the inflation medium including a curable polymer, a liquid, a gas, or combination thereof.

11. The facet implant of claim 10, wherein the inflation medium is selectively removable from the insert to adjust dimensions of the insert.

12. The facet implant of claim 1, wherein the shrink-wrap material includes a polymeric material.

13. The facet implant of claim 1, wherein the shrink-wrap material includes a coating adapted to reduce tissue ingrowth.

14. The facet implant of claim 1, wherein the insert is formed of metal, polymer, ceramic, or combinations thereof.

15. The facet implant of claim 1, wherein the insert contains a therapeutic agent.

* * * * *